(12) United States Patent
Ludwiczak

(10) Patent No.: US 7,770,453 B2
(45) Date of Patent: Aug. 10, 2010

(54) VIBRATING DEBRIS REMOVER

(76) Inventor: Damian R. Ludwiczak, 5989 Churchill Way, Medina, OH (US) 44256

( * ) Notice: Subject to any disclaimer, the term of this patent is extended or adjusted under 35 U.S.C. 154(b) by 244 days.

(21) Appl. No.: 11/858,680

(22) Filed: Sep. 20, 2007

(65) Prior Publication Data

US 2008/0054762 A1  Mar. 6, 2008

Related U.S. Application Data

(63) Continuation-in-part of application No. 11/461,667, filed on Aug. 1, 2006, now Pat. No. 7,459,831, which is a continuation of application No. 10/949,613, filed on Sep. 24, 2004, now Pat. No. 7,084,553.

(60) Provisional application No. 60/550,567, filed on Mar. 4, 2004.

(51) Int. Cl.
  *H02N 21/00* (2006.01)
  *G01N 29/07* (2006.01)
  *G01N 29/12* (2006.01)

(52) U.S. Cl. .............................. 73/583; 73/579; 73/600; 73/658

(58) Field of Classification Search .................... 73/584, 73/583, 579, 600, 602, 658; 310/323.01, 310/328
See application file for complete search history.

(56) References Cited

U.S. PATENT DOCUMENTS 3,008,232 A  11/1961  Shea, Jr.
3,171,683 A  3/1965  Ludwig
3,395,414 A  8/1968  Malin
3,530,577 A  9/1970  Franklin et al.

(Continued)

FOREIGN PATENT DOCUMENTS

DE  296 21 783 U1  5/1998

(Continued)

OTHER PUBLICATIONS

Ultrasound Technology—Aircraft Anti-Icing and Deicing Protection, "Aircraft Anti-Icing and Deicing Protection Using Ultrasound Technology", Website page, May 1997.

*Primary Examiner*—J M Saint Surin
(74) *Attorney, Agent, or Firm*—Hahn Loeser & Parks LLP

(57) ABSTRACT

Embodiments of the present invention relate to a device which may be permanently attached or removably attached to a material such as a vehicular glass window or airplane wing. This device may comprise of a converter sub-unit or vibrator and a coupler. These elements may be arranged to propagate mechanical motion generated by the converter sub-unit through the coupler and optionally into the edge of the attached material. The resulting vibration motion in the material, which could take the form of a longitudinal compression/rarefaction wave, transverse wave, or a combination of the two waveforms, may be of a sufficient magnitude so as to cause the adhesive bond between the material's surface and other solid debris, such as ice, to be broken. This allows the debris to fall away while not damaging the material. The vibration motion in the material may be also of sufficient magnitude to remove a liquid such as water from the material surface. In other embodiments, the device is connected to a pulser/receiver and/or a frequency spectrum electronic unit to function as a debris detector.

9 Claims, 17 Drawing Sheets

U.S. PATENT DOCUMENTS

| | | | |
|---|---|---|---|
| 3,793,723 A | 2/1974 | Kuris et al. | |
| 4,038,571 A | 7/1977 | Hellenkamp | |
| 4,231,155 A | 11/1980 | Johne | |
| 4,286,383 A | 9/1981 | Farden | |
| 4,381,604 A | 5/1983 | Horst | |
| 4,387,973 A | 6/1983 | Martin | |
| 4,432,117 A | 2/1984 | Iskiw | |
| 4,466,851 A | 8/1984 | Hoffman | |
| 4,744,144 A | 5/1988 | Lowery et al. | |
| 4,824,250 A * | 4/1989 | Newman | 356/502 |
| 4,833,373 A | 5/1989 | Doi et al. | |
| 4,858,264 A | 8/1989 | Reinhart | |
| 4,929,072 A | 5/1990 | Fujie et al. | |
| 5,007,722 A | 4/1991 | Mori et al. | |
| 5,037,189 A | 8/1991 | Fujie et al. | |
| 5,136,425 A | 8/1992 | Fujie et al. | |
| 5,148,312 A | 9/1992 | Kawai et al. | |
| 5,170,288 A | 12/1992 | Imaizumi et al. | |
| 5,172,024 A | 12/1992 | Broussoux et al. | |
| 5,287,582 A | 2/1994 | Kawai et al. | |
| 5,323,265 A | 6/1994 | Fujie et al. | |
| 5,394,875 A * | 3/1995 | Lewis et al. | 600/445 |
| 5,475,530 A | 12/1995 | Fujie et al. | |
| 5,548,175 A | 8/1996 | Tamai | |
| 5,724,186 A | 3/1998 | Collier | |
| 5,930,899 A | 8/1999 | Hartman et al. | |
| 6,399,948 B1 * | 6/2002 | Thomas et al. | 250/341.6 |
| 6,743,298 B2 | 6/2004 | Schmid | |
| 6,998,616 B2 * | 2/2006 | Favro et al. | 250/341.6 |
| 7,057,176 B2 * | 6/2006 | Rothenfusser et al. | 250/341.6 |
| 7,084,553 B2 | 8/2006 | Ludwiczak | |
| 7,122,801 B2 * | 10/2006 | Favro et al. | 250/341.6 |
| 7,199,367 B2 * | 4/2007 | Favro et al. | 250/341.6 |
| 2004/0035912 A1 | 2/2004 | Li et al. | |

FOREIGN PATENT DOCUMENTS

| | | |
|---|---|---|
| DE | 198 26 168 A1 | 8/1999 |
| DE | 100 05 341 A1 | 8/2001 |
| DE | 100 33 382 A1 | 1/2002 |
| WO | 2005/086572 A2 | 9/2005 |
| WO | 2005/086572 A3 | 5/2006 |

* cited by examiner

VIBRATING DEBRIS REMOVER

This application is a Continuation-in-Part of U.S. application Ser. No. 11/461,667, filed Aug. 1, 2006 and entitled "Vibrating Debris Remover, which is a Continuation of U.S. application Ser. No. 10/949,613, entitled "Vibrating Debris Remover," now U.S. Pat. No. 7,084,553, which claims the benefit of U.S. Provisional Application Ser. No. 60/550,567, filed Mar. 4, 2004, all of which are hereby incorporated herein by reference.

GOVERNMENT INTEREST

This invention was made by an employee of the Untied States Government. The Government has a nonexclusive, irrevocable, royalty-free license in the invention with power to grant licenses for all governmental purposes.

TECHNICAL FIELD

This invention relates to a device that when attached along the edge of a material, such as a vehicular window, will propagate mechanical vibration or shock motion created by the device into the material with sufficient magnitude in order to remove solid debris, such as ice, and/or liquid debris, such as water, from the surface of the material. The present invention shall be described chiefly with respect to an application for the removal of ice and/or water from the windshield of an automobile. However, it will be easily understood that the described application of the invented device is in no way restrictive to a great many other applications in which the removal of debris from other types of material surfaces may be required. Some examples of other applications include ice removal from aircraft wings, adhesive removal on/or between two materials, cookware cleaning, and the removal of paint from a material surface. Additionally, a pulser/receiver and/or frequency spectrum electronic unit could be attached to the converter sub-unit such that the device could also function as a debris detector.

BACKGROUND OF THE INVENTION

It is important for the safe operation of any vehicle that a clear, unobstructed view to the outside environment be maintained. An example of such viewing need is for the driver of an automobile. In this application, material such as the windshield, side windows, rearview mirrors, and rear windows have a surface exposed to the outside weather elements where rain, snow, ice, and other debris can accumulate. The accumulation of this debris poses a significant problem with maintaining a clear view to the outside environment.

In an attempt to maintain a clear view to the outside environment, a device utilizing mechanical motion has been developed. This device, which is either removable or permanently attached to the edge of a material, is comprised of two elements, a converter sub-unit and an amplifying coupler sub-unit. The converter sub-unit converts an energy source such as electrical, pneumatic, or fluid into mechanical vibration or shock pulse motion. The amplifying coupler sub-unit transfers the mechanical motion generated by the converter sub-unit into the attached material. Also, the amplifying coupler sub-unit can be designed to reduce, magnify, or keep constant the amplitude of the converter sub-unit mechanical motion before it enters the material.

In prior art, one method used to remove solid debris such as ice from a material surface consists of a device which blows hot air on the material's interior surface or heats the material surface by the Joule effect through metal wires attached to the material. A major drawback to these devices is that the time it takes to remove the debris is significant. Also, the field of view is obstructed with the metal wire technology.

In other prior art, another method used to remove debris such as ice and/or liquid from a material surface consists of mounting transducer elements, which vibrate, directly onto the material surface. The transducer elements are made from piezoelectric or magnetostrictive material and electrical energy is used to make these elements vibrate. A major drawback of these devices is that the vibrating transducer elements mount perpendicular and directly on the material surface. Because the vibrating transducer elements are attached in this manner, the magnitude of the vibrations developed by the transducer elements cannot be altered, and in particular magnified, prior to entering into the material. This results in a design which is very inefficient because of the amount of energy required to generate the necessary vibration amplitude in the material to remove the unwanted debris. Another drawback of these devices is that the dimensions of the vibrating transducer piezoelectric or magnetostrictive elements have to be carefully chosen such that their natural vibration frequency is tuned to that of the material in order that the device works efficiently. Additionally, some of the above referenced devices are mounted on the material surface in such a way that the field of view through the material can be highly obstructed if applied in the use of windshield or side windows for removing debris.

SUMMARY OF THE INVENTION

One embodiment of the present invention may comprise a device having two elements, a converter sub-unit and an amplifying coupler sub-unit. These two elements may used together to efficiently propagate mechanical motion or vibrations into, for example, an edge of a material, causing the material to vibrate. Because the material may vibrate with sufficient displacement and acceleration, the removal of the debris is achieved by breaking the adhesive bond existing between the material and the undesired debris. This may be done without harming the material and without obstructing the view through the material.

Therefore, an embodiment of the present invention provides a system for removing ice, water, or other debris from a material, by causing vibrational motion to occur in the material. The vibrations in the material may be the result of mechanical vibration or a shock pulse motion entering into the edge of the material through the use of an amplifying coupler sub-unit. Another embodiment of the present invention may provide a debris removal system in which the vibration frequency is adjustable, if required, for matching the resonating vibration frequency of the material with debris attached.

In yet another embodiment, a debris removal system may be operably associated with a pulser/receiver unit and/or a frequency spectrum electronic unit. In this embodiment, the device could function as a debris sensor by analyzing the time difference between sending out a vibration and receipt of the corresponding electric signal that is generated by reflective vibrations vibrating the piezoelectric crystal, or by analyzing the frequency spectrum of the electric signal generated by the reflected vibrations vibrating the piezoelectric crystal. The time shift of the vibrations and/or frequency spectrum of the resulting electric signal may be compared to a known values of the same generated in the material with no debris attached. A deviation from the known values may indicated that debris is present.

DETAILED DESCRIPTION

The concern for the removal of debris from a material is very real. The present invention shall be described with respect to an automotive windshield. However, this should in no way be restrictive, as a great many other materials and applications exist to which this invented debris removal device could be employed.

Figure 1:
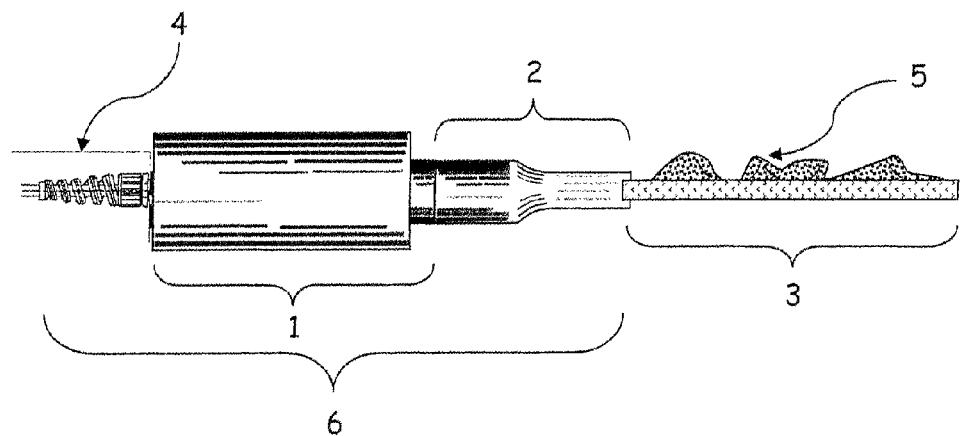
FIG. 1 is a side view of a Vibrating Debris Remover attached to a material with debris, in accordance with a preferred embodiment of the present invention.
Figure 2:
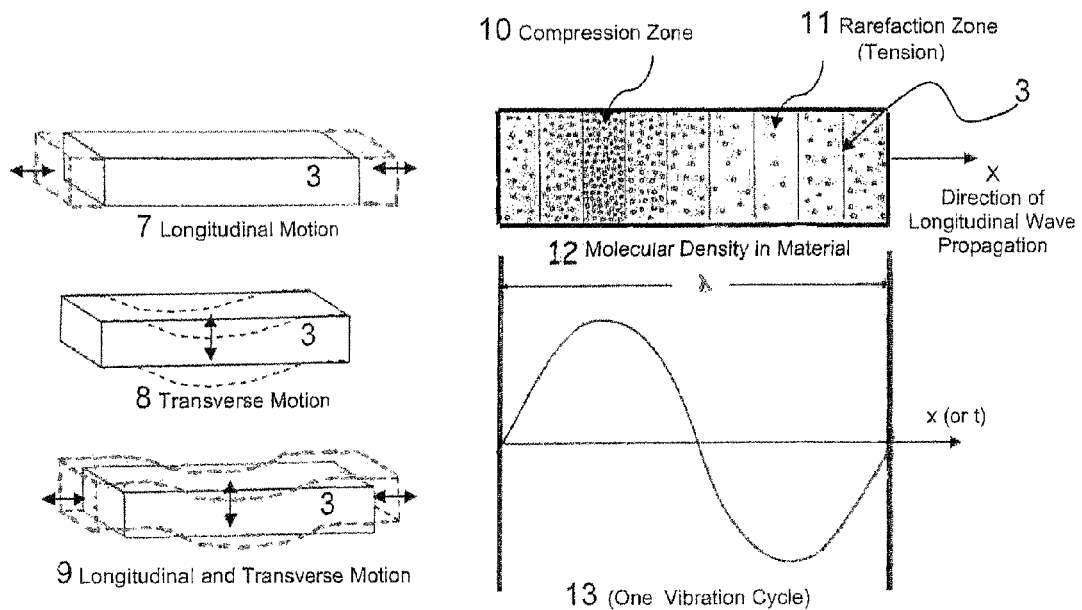
FIG. 2 is a schematic view showing various types of mechanical vibration waveforms present in material.

As shown in FIG. 1, some type of debris 5, such as ice and or water, can build on a material 3 surface, such as an automobile windshield, to a level where visibility to the outside environment is impaired. This results in a dangerous operating condition. A vibrating debris remover 6 has been invented that can remove debris 5, such as ice, from a material 3 surface, such as an automotive windshield 40 or aircraft airframe 43. The vibrating debris remover 6 consists of two parts, the converter sub-unit 1 and the amplifying coupler sub-unit 2 to which the material 3 is attached.

The converter sub-unit 1 and amplifying coupler sub-unit 2 are so arranged as to propagate mechanical vibration or shock pulse motion generated by the converter sub-unit 1 into the amplifying coupler sub-unit 2 and then into the edge of the material 3. The amplifying coupler sub-unit 2 can be designed to reduce, magnify, or keep constant the amplitude of the converter sub-unit's 1 mechanical vibration or shock pulse motion before it enters the material 3 to which is attached some debris 5 particle.

The resulting vibrations 13 in the material 3 will be in the form of a longitudinal 7 motion, transverse 8 motion, or a combination 9 of the two based on how the amplifying coupler sub-unit 2 is attached to the material 3. The longitudinal 7 motion in the material 3 is the result of compressions 10 and rarefactions 11 in the material's molecular density 12 and is only in the direction of the propagating vibrations. The longitudinal 7 motion requires a change in the volume or molecular density 12 of the material 3. The transverse 8 motion is perpendicular to the direction of the propagating vibrations and is a result of shear stresses in the material 3. The longitudinal 7 motion, transverse 8 motion, or a combination 9 of the two in the material 3 is of a sufficient magnitude and strain rate such that the adhesive bond between the material 3 and debris 5 is quickly broken allowing the debris 5 to fall away while not damaging the material 3. The vibrations 13 (showing the shift in molecular density as a function of position, x, or time, t, for a single wavelength λ) in the material 3 are also of sufficient magnitude as to cause water droplets 5 to leave the material 3 surface.

1.0 Converter Sub-Unit

Figure 3:
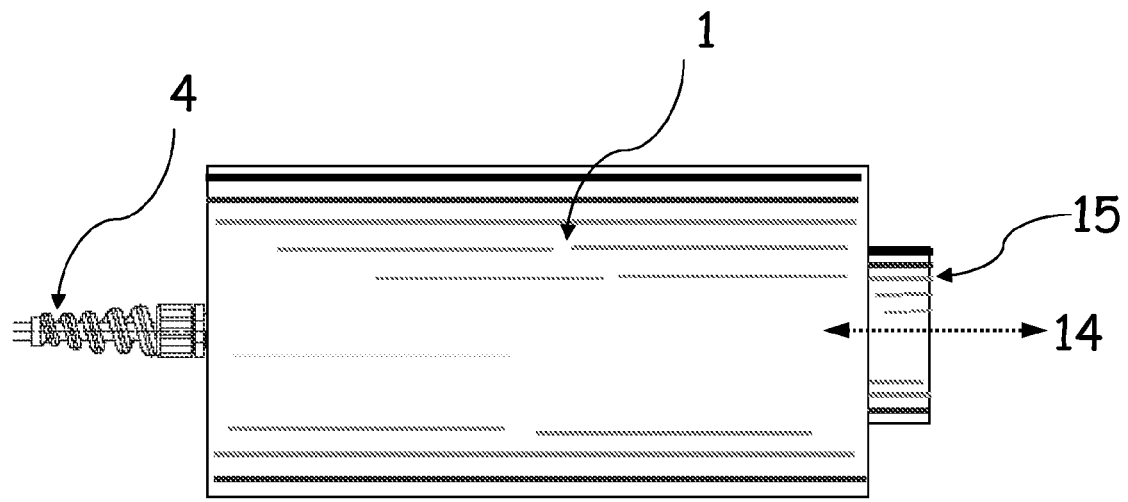
FIG. 3 is a side view of a preferred embodiment of a Vibrating Debris Remover converter sub-unit.
Figure 4:
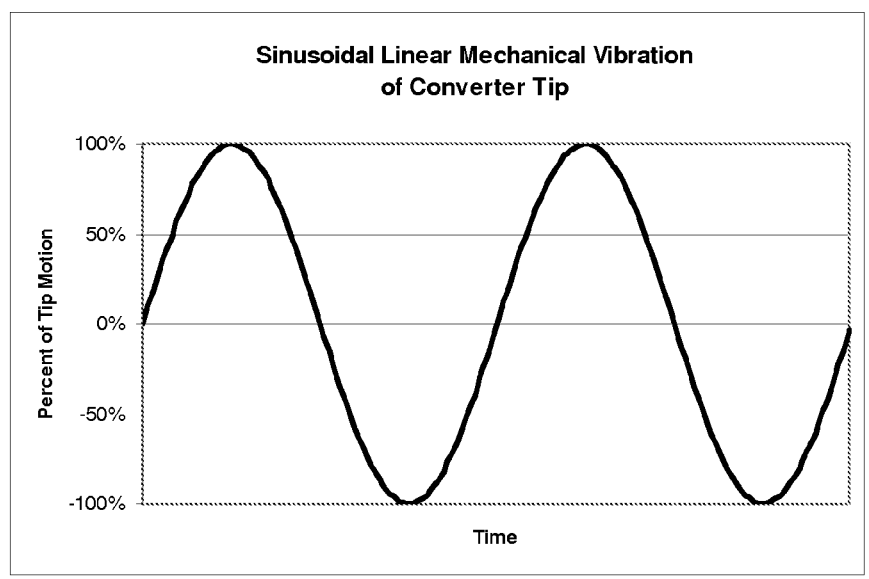
FIG. 4 is a graphic representation illustrating sinusoidal vibration motion at the converter sub-unit tip.
Figure 5:
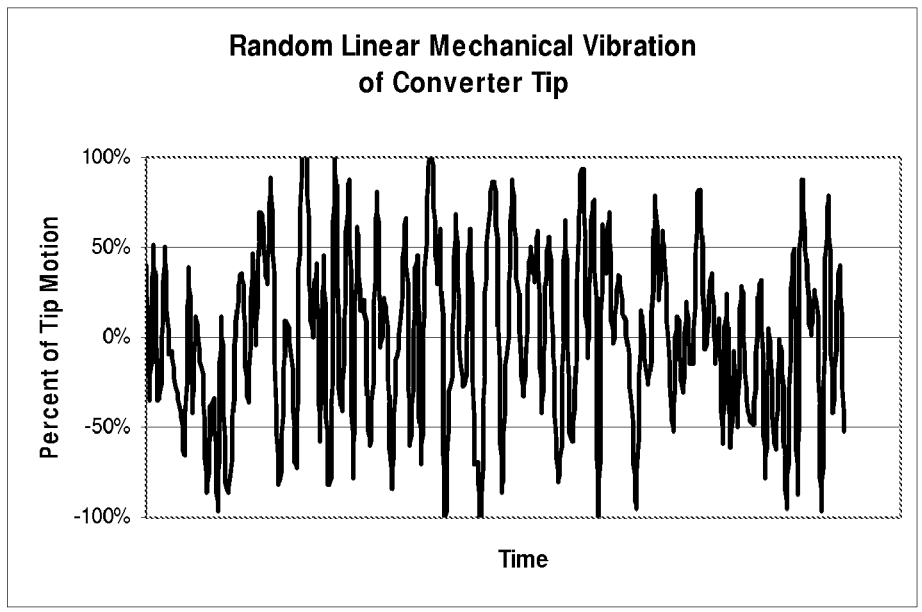
FIG. 5 is a graphic representation illustrating random vibration motion at the converter sub-unit tip.
Figure 6:
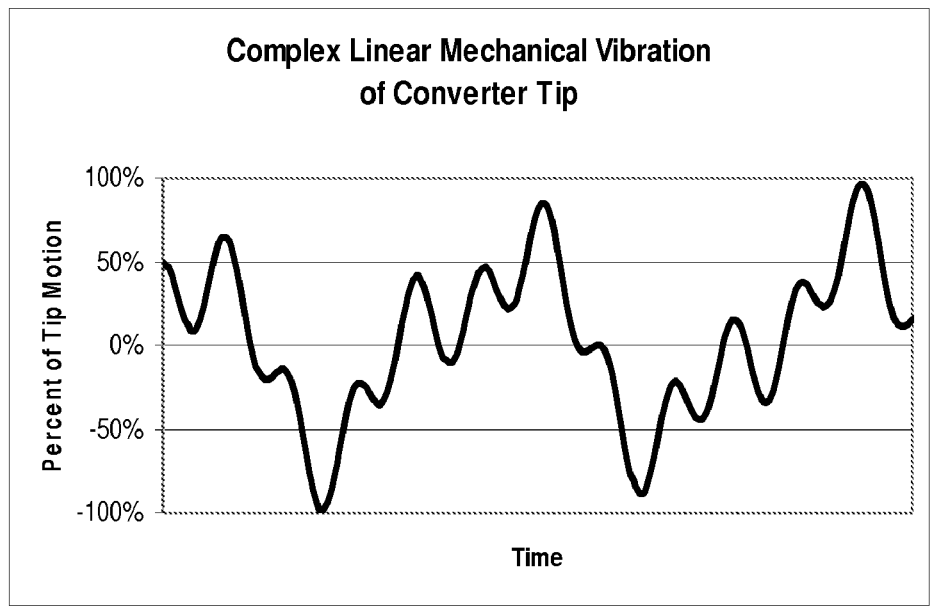
FIG. 6 is a graphic representation illustrating complex vibration motion at the converter sub-unit tip.
Figure 7:
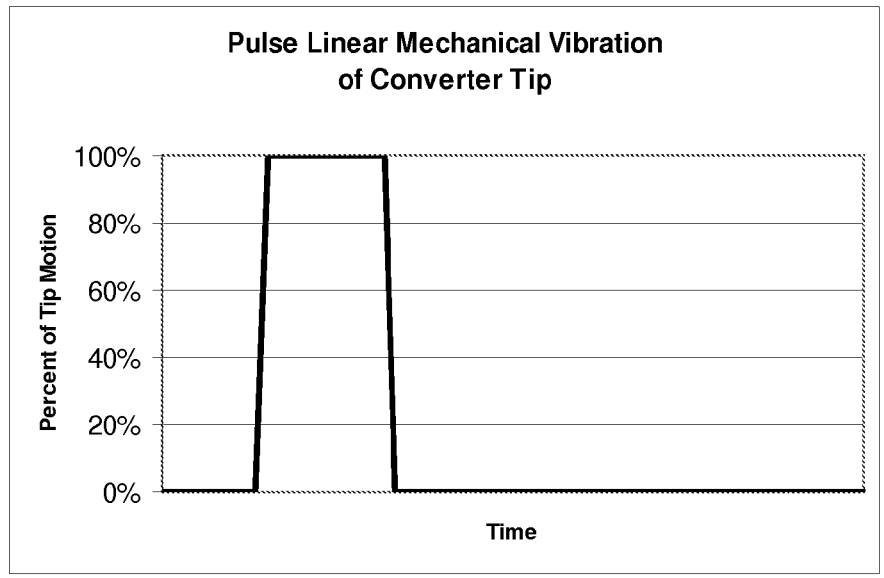
FIG. 7 is a graphic representation illustrating shock pulse vibration motion at the converter sub-unit tip.

As shown in FIG. 1 and FIG. 3, the converter sub-unit 1 has the purpose of converting an external energy source 4 such as electrical, pneumatic, or fluid into longitudinal mechanical motion 14 at the converter sub-unit tip surface 15. For example, the longitudinal mechanical motion 14 of the converter sub-unit tip surface 15 could take the form of a sine wave (FIG. 4), random wave (FIG. 5), complex wave (FIG. 6), or a pulse wave (FIG. 7). In addition, the longitudinal mechanical motion 14 of the converter sub-unit tip surface 15 could be a combination of all or some of the above mentioned waveforms.

Figure 8:
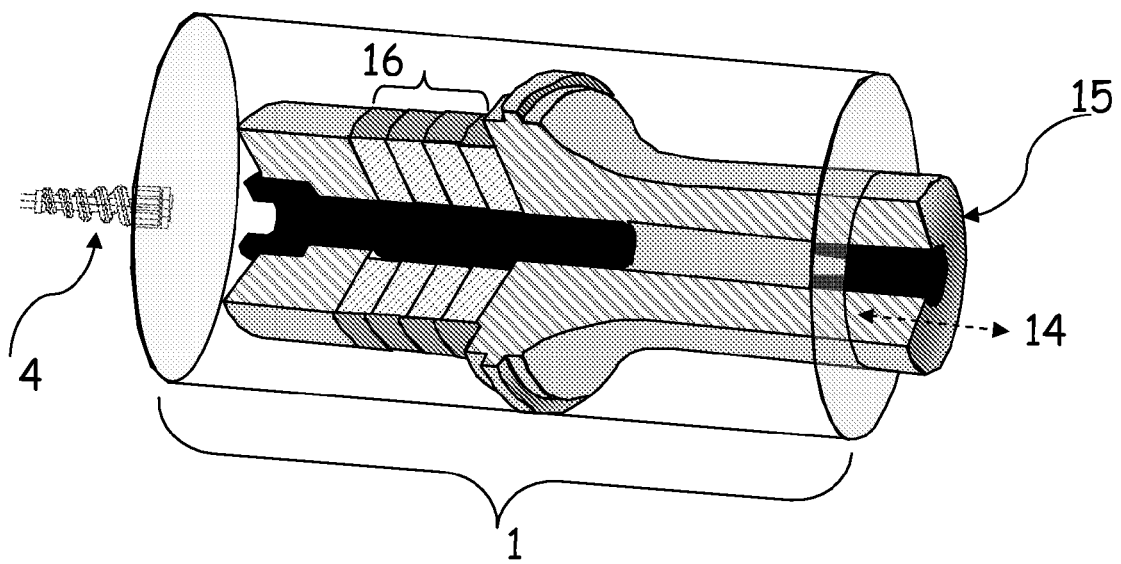
FIG. 8 is a schematic view illustrating a Vibrating Debris Remover piezoelectric converter sub-unit.

There are several devices in existence which can perform the function of the converter sub-unit 1. As an example, an electrical energy source 4 can be converted into longitudinal mechanical vibration motion 14 of the converter sub-unit's acoustic transformer surface 15 through the use of a piezoelectric transducer consisting of piezoelectric material 16 as shown in FIG. 8. An electrical oscillator energy source 4 is passed to the piezoelectric material via electrodes causing the piezoelectric material 16 to expand and contract (i.e. vibrate). As the piezoelectric material 16 expands and contracts, it pushes against an acoustic transformer, causing the acoustic transformer surface 15 to vibrate. Electrical energy 4 can also be converted into longitudinal mechanical vibration motion 14 of the converter sub-unit tip surface 15 through the use of a magnetostrictive transducer.

An electrical energy source 4 can also be converted into longitudinal mechanical vibration motion 14 of the converter sub-unit tip surface 15 through the use of an electric motor and gearing.

As a further example, a pneumatic energy source 4 can be converted into longitudinal mechanical vibration motion 14 of the converter sub-unit tip surface 15 through the use of a pneumatic hammer.

As a final example, longitudinal mechanical vibration motion 14 of the converter sub-unit tip surface 15 can be created through the use of whistles and sirens which use a fluid jet energy source 4, such as compressed air, to pass through an orifice, causing the converter sub-unit tip surface 15 to vibrate.

As an example of a device that can create a longitudinal mechanical shock pulse motion, an electrically activated solenoid can be used to cause the movement of a plunger component. This plunger component can be a metal rod such that when it contacts another surface, a shock pulse is created which travels into the contacting surface 17 such as the one on the amplifying coupler sub-unit 2.

2.0 Converter Sub-Unit to Amplifying Coupler Sub-Unit Attachment

Figure 9:
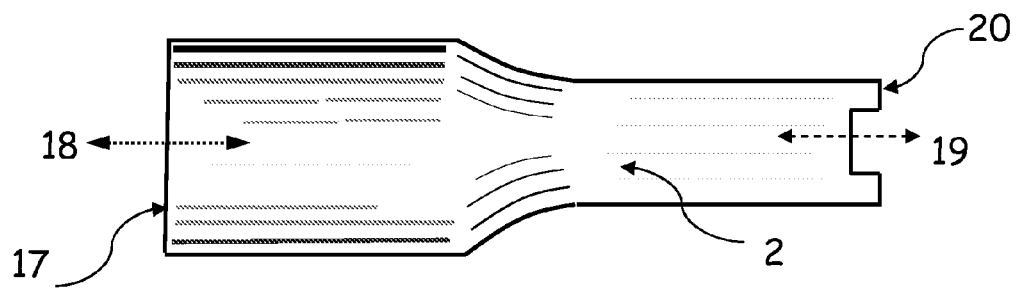
FIG. 9 is a side view of an amplifying coupler sub-unit with stepped geometry, in accordance with a preferred embodiment of the present invention.

The converter sub-unit tip surface 15 is in contact with the amplifying coupler sub-unit surface 17, an example of which is shown in FIG. 9. These two surfaces are connected to each other in such a fashion to ensure that the longitudinal mechanical vibration and/or shock pulse motion 14 from the converter sub-unit tip surface 15 transfers into the amplifying coupler sub-unit surface 17. This causes the amplifying coupler sub-unit surface 17 to have longitudinal vibration motion 18 which transfers through the amplifying coupler sub-unit 2 and creates longitudinal mechanical vibration and/or shock pulse motion 19 at the amplifying coupler sub-unit tip surface 20.

Figure 10:
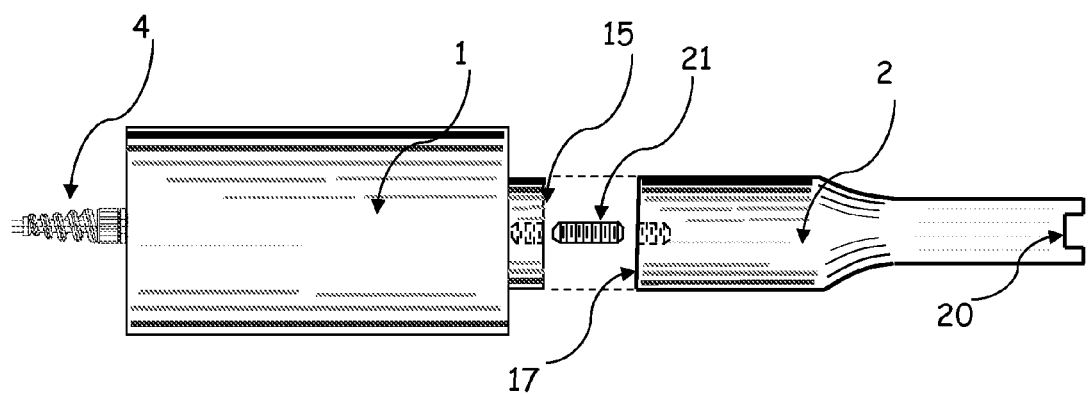
FIG. 10 is a side exploded view of a converter sub-unit connected to an amplifying coupler sub-unit via a threaded stud fastener.

For example, as shown in FIG. 10, the connection could be made with an inserted threaded stud 21. Attachment of the converter sub-unit 1 and the amplifying coupler sub-unit 2 onto the threaded stud 21 is made such that the converter sub-unit tip surface 15 and the amplifying coupler sub-unit surface 17 are placed and remain in compression. This configuration results in a design which the converter sub-unit 1 can be removed and replaced relatively easily.

Figure 11:
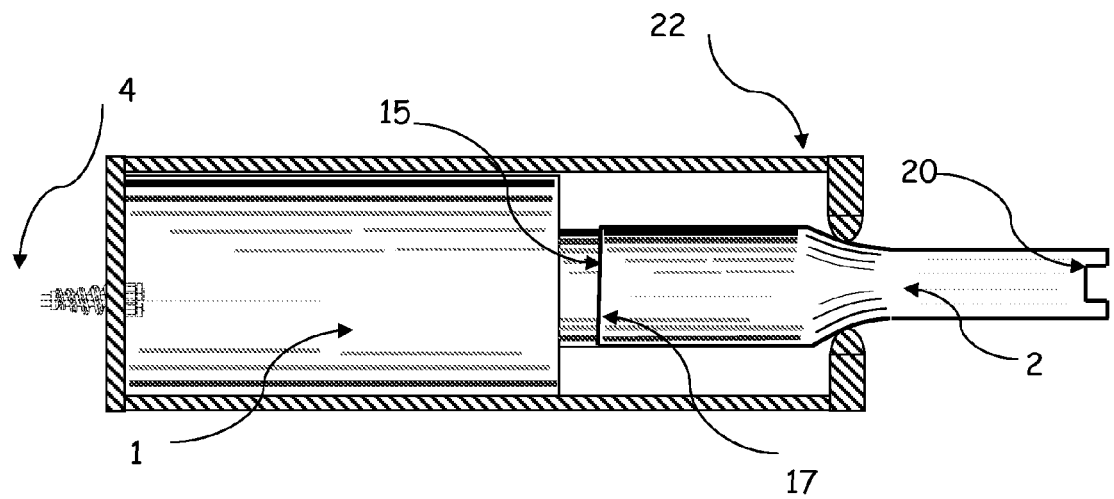
FIG. 11 is a partial cross-sectional view of a converter sub-unit connected to an amplifying coupler sub-unit via a support frame.

As an additional example, as shown in FIG. 11, the converter sub-unit tip surface 15 and the amplifying coupler sub-unit surface 17 could be placed in compression by pushing the converter sub-unit tip surface 15 up against the amplifying coupler sub-unit surface 17 through the use of a clamping device 22 such that the converter sub-unit tip surface 15 and the amplifying coupler sub-unit surface 17 are placed and remain in compression. This configuration also results in a design which the converter sub-unit 1 can be removed and replaced.

Figure 12:
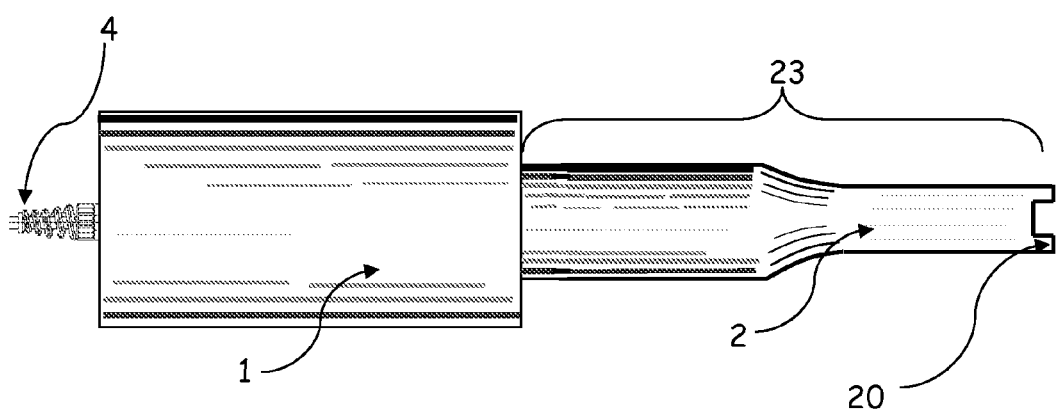
FIG. 12 is a side view illustrating a converter sub-unit and amplifying coupler sub-unit made from same material, in accordance with a preferred embodiment of the present invention.

As shown in FIG. 12, the converter sub-unit tip surface 15 and amplifying coupler sub-unit surface 17 could be made nonexistent because the converter sub-unit 1 and the amplifying coupler sub-unit 2 are made from a single piece of material 23. In this arrangement, the converter sub-unit 1 would not be removable from the amplifying coupler sub-unit 2. This configuration results in a design that would create a more difficult maintenance situation if the converter sub-unit 1 had to be replaced.

3.0 Converter Sub-Unit to Amplifying Coupler Sub-Unit Material Matching

In addition to an interface that can transfer motion between the converter sub-unit tip surface 15 and the amplifying coupler sub-unit surface 17, it is also advantageous to understand what impedance values exist between the materials used for the converter sub-unit 1 and the amplifying coupler sub-unit 2. By understanding the material impedances, the values of the stress wave reflection and stress wave transmission coefficients can be calculated at the interface of the converter sub-unit tip surface 15 to the amplifying coupler sub-unit surface 17. The longitudinal mechanical vibration and/or shock pulse motion 14 of the converter sub-unit tip surface 15 is transferred by a force from the converter sub-unit tip surface 15 pushing up against the amplifying coupler sub-unit surface 17. Since this force is acting through the cross sectional area of the converter sub-unit tip surface 15, a stress state is present at this interface.

This stress state is important to know because there are cases in which the longitudinal mechanical vibration and/or shock pulse motion 14 of the converter sub-unit tip 15 does not create any substantial longitudinal mechanical vibration and/or shock pulse motion 18 at the amplifying coupler sub-unit surface 17. This condition exists if there is a significant difference between the impedance values of the converter sub-unit 1 and amplifying coupler sub-unit 2 materials. The result is a very inefficient design and the amount of energy 4 required for the converter sub-unit 1 to remove debris 5 on the material surface 3 would be unreasonably high.

Figure 13:
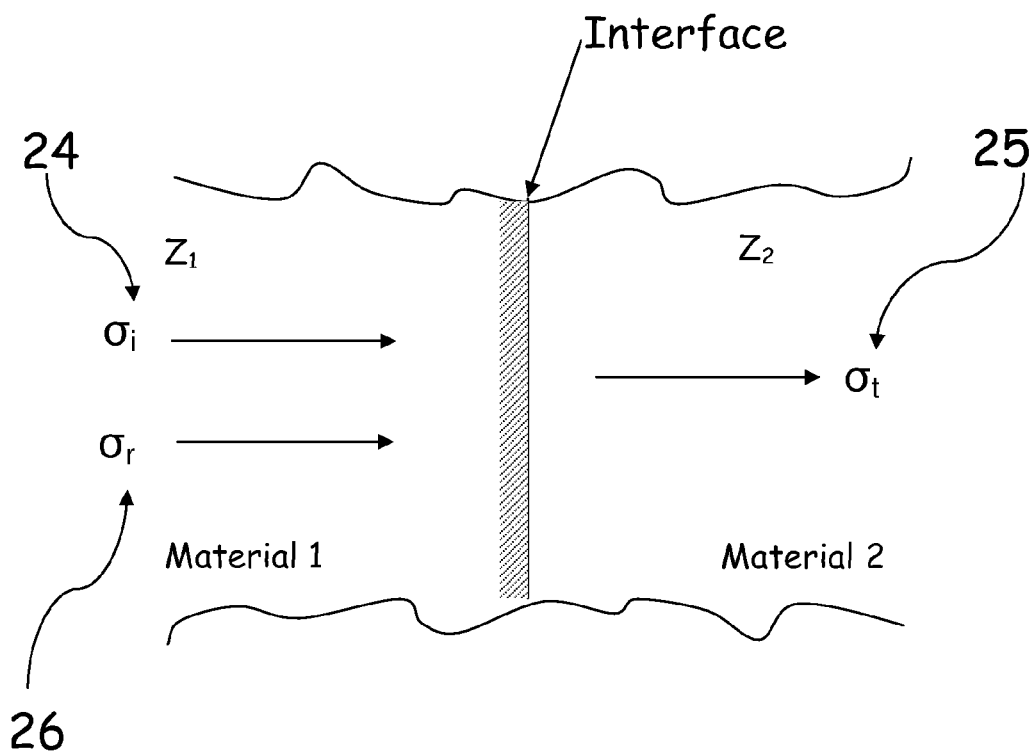
FIG. 13 is a schematic representation illustrating stress transmission definition across an interface.

Referring to FIG. 13 and assuming that the converter sub-unit tip surface 15 and the amplifying coupler sub-unit surface 17 have identical cross sectional areas, mathematical equations (1) and (2) can be used to determine the stress transmission and stress reflection coefficients at this interface.

$$r = \frac{Z_2 - Z_1}{Z_2 + Z_1} \qquad \text{Equation (1)}$$

$$t = \frac{2Z_2}{Z_2 + Z_1} \qquad \text{Equation (2)}$$

Where:
r=the stress reflection coefficient
t=the stress transmission coefficient
$Z_1$=impedance of material 1

$Z_2$=impedance of material 2

Using equations (1) and (2), it can be shown that if the material properties of the converter sub-unit and amplifying coupler sub-unit are the same, then $Z_1=Z_2$, the stress reflection coefficient is zero, and the stress transmission coefficient is one. This means that the incident stress wave 24 is completely transmitted with no reflected stress wave 26. The incident stress wave 24 and the transmitted stress wave 25 have the same magnitudes.

However, if $Z_1>Z_2$, it can be shown using equations (1) and (2) that the magnitude of the transmitted stress wave 25 will have less magnitude than the original incident stress wave 24. In addition, the reflected stress wave 26 will have a negative value. This means that an incident stress wave 24 that is compressive 10 in nature will be reflected 26 as a rarefaction 11 and that an incident stress wave 24 that is a rarefaction 11 in nature will be reflected 26 as a compressive 10 wave.

Also notice that if $Z_1<Z_2$, it can be shown using equations (1) and (2) that the stress reflection coefficient is greater than a value of zero and the stress transmission coefficient is greater than a value of one. This means that the incident stress wave 24 is amplified through the joint and that the transmitted stress wave 25 has a higher magnitude than the incident stress wave 24.

By choosing the proper materials for the converter sub-unit 1 and amplifying coupler 2, an efficient transfer of stress 25 can be achieved at the converter sub-unit tip surface 15 to amplifying coupler surface 17.

4.0 Amplifying Coupler Sub-Unit

Figure 14:
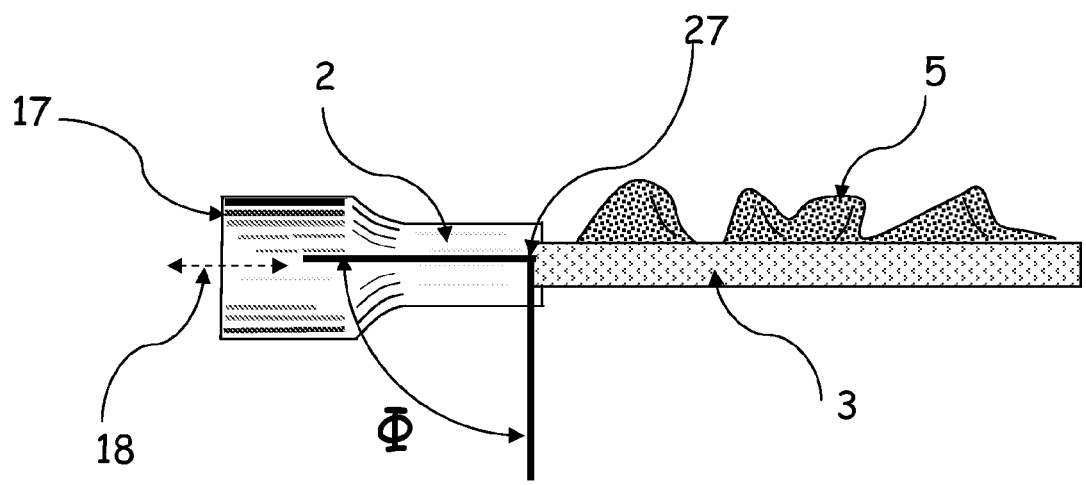
FIG. 14 is a side schematic view illustrating amplifying coupler sub-unit-to-material connection definitions.

The amplifying coupler sub-unit 2 has the purpose of transmitting the converter sub-unit's 1 longitudinal mechanical vibration and/or shock pulse motion 14 into the edge 27 of the material 3. There are several advantages to using an amplifying coupler sub-unit 2. These advantages are: (I) the converter sub-unit 1 can be easily removed for repairs and also easily installed, (II) the amplifying coupler sub-unit 2 can serve as an impedance buffer to better match that of the converter sub-unit tip 15 material to that of the material 3 with attached debris, (III) the amplifying coupler sub-unit 2 can be designed to reduce, magnify, or keep constant the amplitude of the converter sub-unit's 1 mechanical motion 14 before it enters the material 3, (IV) it can direct the longitudinal mechanical vibration and/or shock pulse motion developed by the converter sub-unit 1 in a direction which is not the same as the longitudinal mechanical vibration and/or shock pulse motion direction in the material 3, and (V) the amplifying coupler sub-unit 2 can be specially designed to attach to the material 3 edge 27 as shown in FIG. 14.

As an example to explain how the amplifying coupler sub-unit 2 can be designed to serve as an impedance buffer, or how it can be designed to reduce, magnify, or keep constant the amplitude of the converter sub-unit's 1 mechanical motion 14 before it enters the material 3, mathematical equations (3) and (4) can be used.

Figure 15:
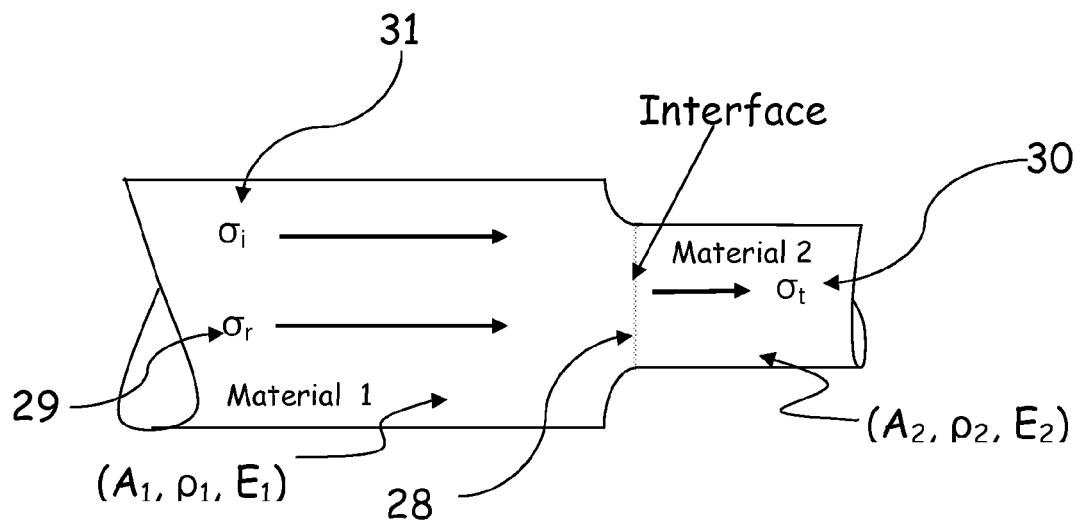
FIG. 15 is a schematic view illustrating an amplifying coupler sub-unit with stepped geometry stress transmission definition.

Referring to FIG. 15 and equations (3) and (4) the knowledge of how stress will transfer through an interface 28 of two different materials and a step in cross sectional areas is presented. FIG. 15 represents a side view of an amplifying coupler sub-unit 2 that utilizes a step change in height along its length.

These equations take into account driving point impedances, differences of material properties, and cross sectional areas to determine the relationship between the incident, reflected, and transmitted stress waves.

These equations are:

$$\sigma_t = \frac{2\left(\frac{Z_2^*}{Z_1^*}\right)\left(\frac{A_1}{A_2}\right)}{1+\left(\frac{Z_2^*}{Z_1^*}\right)}\sigma_i \quad \text{Equation (3)}$$

$$\sigma_r = \frac{\left(\frac{Z_2^*}{Z_1^*}\right)-1}{1+\left(\frac{Z_2^*}{Z_1^*}\right)}\sigma_i \quad \text{Equation (4)}$$

Where:
$\sigma_i$=the incident stress 31 (traveling in material 1 toward material 2)
$\sigma_r$=the stress reflection 29 back into material 1
$\sigma_t$=the stress transmitted 30 into material 2
$Z^*_1$=driving point impedance of material 1
$Z^*_2$=driving point impedance of material 2
$A_1$=cross sectional area of material 1
$A_2$=cross sectional area of material 2

And since force balance at the interface 28 must be maintained, the following force balance relationship must be achieved:

$$A_1(\sigma_i)=A_2(\sigma_t)-A_1(\sigma_r) \quad \text{Equation (5)}$$

Figure 16:
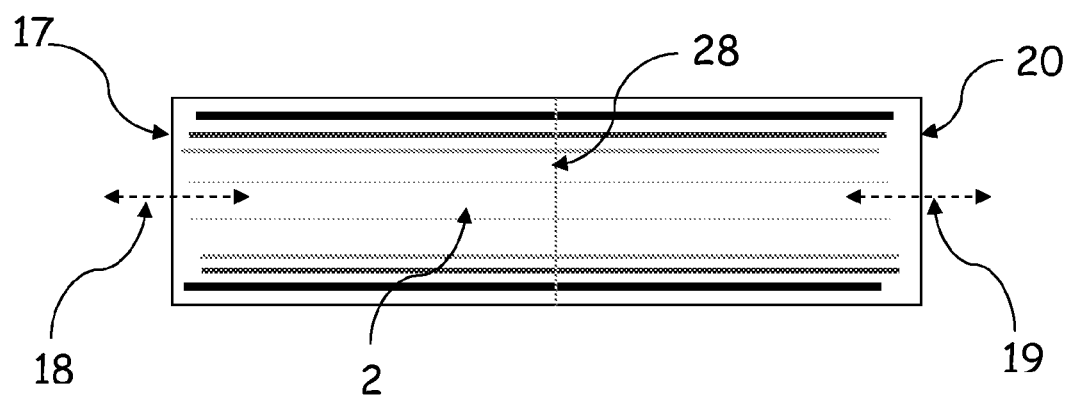
FIG. 16 is a side view of an amplifying coupler sub-unit with no stepped geometry, in accordance with a preferred embodiment of the present invention.

4.1 Example of an Amplifying Coupler Sub-Unit of a Single Material and No Step Change in Area Since in this case the amplifying coupler sub-unit 2 is made of a single material, $Z^*_1=Z^*_2$. Referring to FIGS. 15 and 16 and using equations (3) and (4), it is shown that as long as there is no cross sectional area changes in the amplifying coupler sub-unit 2, there will be no reflected stress wave 29. Also, the transmitted stress wave magnitude 30 is equal to the incident stress wave 31. Thus the longitudinal mechanical vibration and/or shock pulse motion 18 at the amplifying coupler sub-unit surface 17 and the longitudinal mechanical vibration and/or shock pulse motion 19 present at the amplifying coupler sub-unit tip surface 20 will have the same magnitude. Using equation (5), force balance across the interface 28 is maintained.

In reality there will be some damping losses in the amplifying coupler sub-unit 2 which will cause the longitudinal mechanical vibration and/or shock pulse motion 19 at the amplifying coupler sub-unit tip 20 to be lower in magnitude than the longitudinal mechanical vibration and/or shock pulse motion 18 at the amplifying coupler sub-unit surface 17. However, the material damping loss factors can be minimized.

Figure 17:
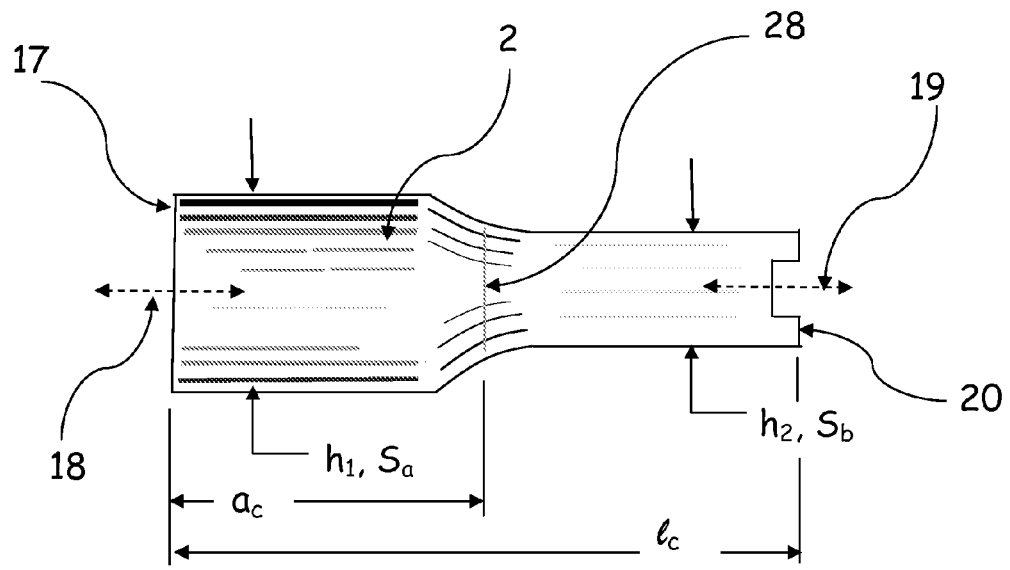
FIG. 17 is a side schematic view of an amplifying coupler sub-unit with stepped geometry; area $A_1$>area $A_2$, in accordance with a preferred embodiment of the present invention.

4.2 Example of an Amplifying Coupler Sub-Unit of a Single Material with a Step Change in Area Referring to FIGS. 15 and 17 and using equations (3) and (4), it is shown that if the amplifying coupler sub-unit 2 has a cross sectional area change in which cross sectional area $A_1$ (which is a function of the diameter or thickness dimension $h_1$) is larger than cross sectional area $A_2$ (which is a function of the diameter or thickness dimension $h_2$), the amplifying coupler sub-unit will have a reflected stress wave 29 that has a magnitude that is less than the incident stress wave 31 and will have the opposite sign of the incident wave. This opposite sign means that an incident compressive stress wave is reflected as a rarefaction (tension) stress wave and an incident rarefaction stress wave is reflected as compression stress wave. The transmitted stress wave 30 will be greater in magnitude than the incident stress wave 31. As a check, the force balance of equation (5) is maintained.

Figure 18:
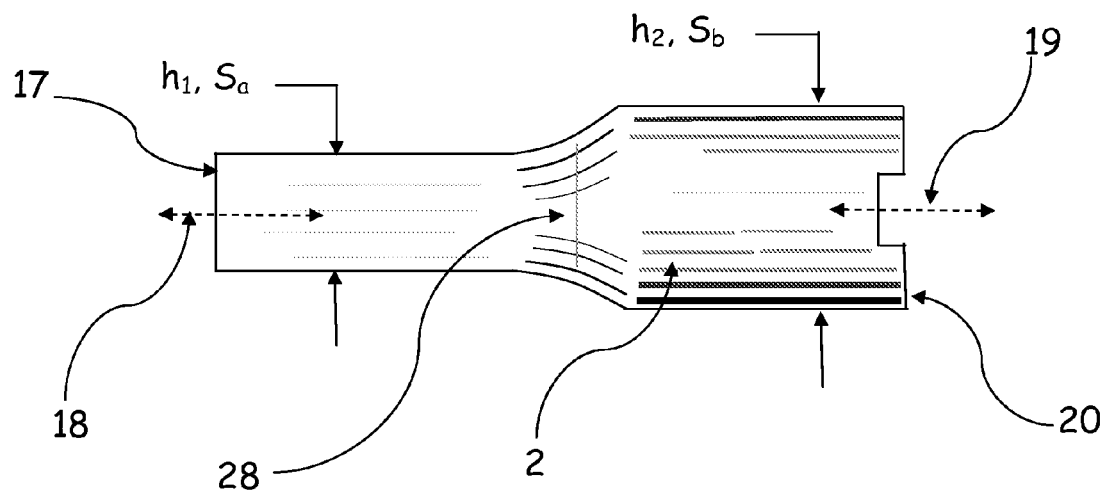
FIG. 18 is a side schematic view of an amplifying coupler sub-unit with stepped geometry; area $A_1$<area $A_2$, in accordance with a preferred embodiment of the present invention.

Referring to FIGS. 15 and 18 and using equations (3) and (4), it is shown that if the amplifying coupler sub-unit 2 has a cross sectional area change in which cross sectional area $A_1$ (which is a function of the diameter or thickness dimension $h_1$) is smaller than cross sectional area $A_2$ (which is a function of the diameter or thickness dimension $h_2$), the amplifying coupler sub-unit will have a reflected stress wave 29 that has a magnitude which is less than the incident stress wave 31 and will have the same sign of the incident wave. This same sign means that an incident compressive stress wave is reflected as a compressive stress wave and an incident rarefaction (tension) stress wave is reflected as rarefaction stress wave. The transmitted stress wave 30 will be smaller in magnitude than the incident stress wave 31. As a check, the force balance of equation (5) is maintained.

As can be seen from equations (3) and (4), there are a great many combinations of material driving point impedances and area ratios that could be used in designing the stepped amplifying coupler sub-unit 2. However, it can be stated that if the stepped amplifying coupler sub-unit 2 is made of a single material and there is a step change in height along the amplifying coupler sub-unit such that $A_1 > A_2$ and since stress is proportional to displacement, then the magnitude of the longitudinal mechanical vibration and/or shock pulse motion 19 of the amplifying coupler sub-unit tip surface 20 will be greater than the longitudinal mechanical vibration and/or shock pulse motion 18 of the amplifying coupler sub-unit surface 17 based only on these parameters.

4.3 Other Types of Amplifying Coupler Sub-Unit Geometries

Figure 19:
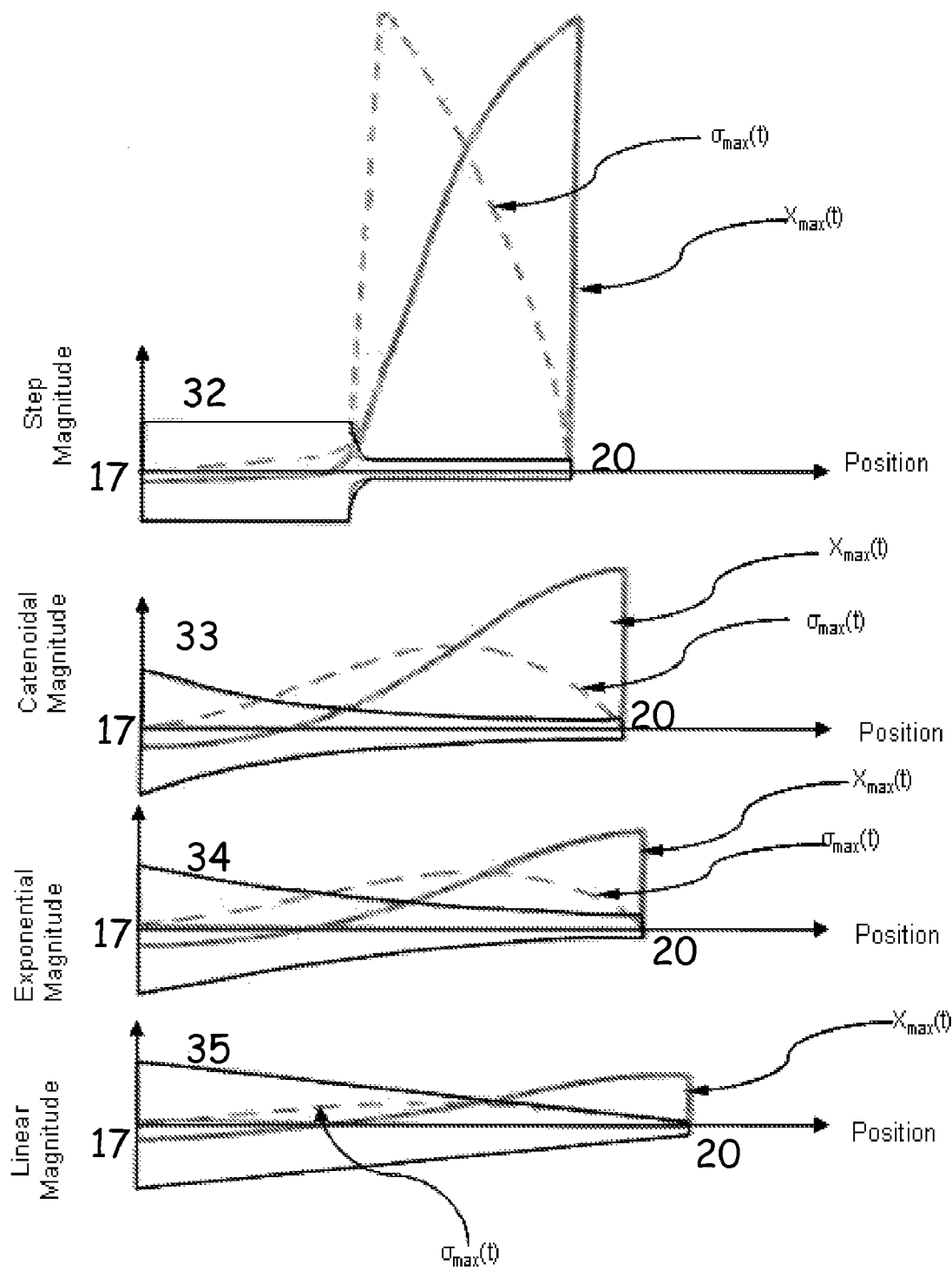
FIG. 19 is a graphical representation illustrating examples of amplifying coupler sub-unit geometries.

There are other amplifying coupler sub-unit 2 designs that do not utilize a step change in area along the amplifying coupler sub-unit 2 length to amplify the longitudinal mechanical vibration and/or shock pulse motion 18 of the amplifying coupler sub-unit surface 17. These designs still have a change in height between the amplifying coupler sub-unit surface 17 and the amplifying coupler sub-unit tip surface 20 but utilize other geometries to achieve this. As examples of these other geometries, FIG. 19 shows the side views of amplifying coupler sub-units 2 that have the following geometries: step 32, catenoidal 33, exponential 34, and linear taper 35. FIG. 19 also shows how the maximum displacements $X_{max}(t)$ and internal material stresses $\sigma_{max}(t)$ vary along the length of the amplifying coupler sub-unit 2.

There are many choices for the amplifying coupler sub-unit geometries. Several engineering text books are available that go into great detail as to how to calculate engineering parameters such as displacement and internal material stress of amplifying coupler sub-units 2 that have various geometric properties.

5.0 Amplifying Coupler Sub-Unit to Material Surface Attachment

The amplifying coupler sub-unit tip surface 20 is in contact with the edge 27 of the material 3. These two surfaces are connected to each other in such a fashion as to ensure that the longitudinal mechanical vibration and/or shock pulse motion 19 from the amplifying coupler sub-unit tip surface 20 transfers into the material 3 of interest causing the material to vibrate 36 with a longitudinal 7, transverse 8, or both a longitudinal and transverse motion 9.

The amplifying coupler sub-unit 2 can be connected to the material 3 at some angle, $\Phi$, as shown in FIG. 14. If the amplifying coupler sub-unit is attached parallel, $\Phi=0°$, to the material surface, then a longitudinal wave 7 will be present in the material 3. If the amplifying coupler sub-unit 2 is connected to the material 3 such that $0°<\Phi<90°$, then a longitudinal and transverse wave 9 will be present in the material 3. If the amplifying coupler sub-unit is attached perpendicular, $\Phi=90°$, to the surface, then a transverse wave 8 will be present in the material 3. In any attachment configuration, consideration must be given to ensure that the vibration 36 resulting in the material is sufficient to break the adhesive bond between the debris 5 and the material 3 surface.

Figure 21:
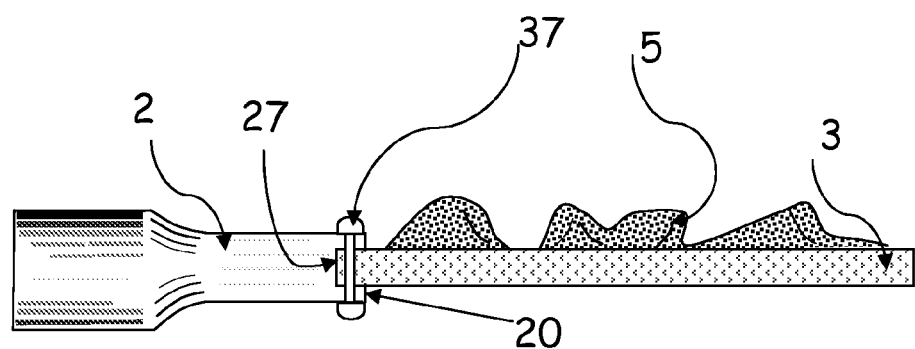
FIG. 21 is a side, partially cross-sectional, view of an amplifying coupler sub-unit connected to material via a fastener, in accordance with a preferred embodiment of the present invention.

For example, as shown in FIG. 21, the connection could be made with an inserted fastener 37 attaching the amplifying coupler sub-unit 2 and the material 3 together such that the amplifying coupler sub-unit tip surface 20 and the material edge 27 are preferably placed and remain in compression.

Figure 22:
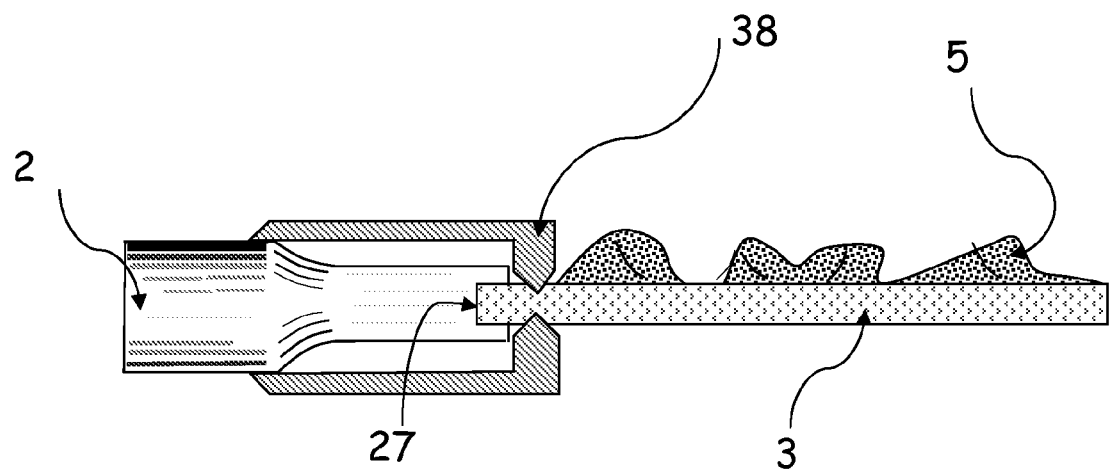
FIG. 22 is a side, partially cross-sectional, view of an amplifying coupler sub-unit connected to material via a support frame, in accordance with a preferred embodiment of the present invention.

Additionally, as shown in FIG. 22, the amplifying coupler sub-unit tip surface 20 and the material edge 27 could be placed and remain in compression by pushing the amplifying coupler sub-unit tip surface 20 up against the material edge 27 through the use of a clamping device 38 such that the amplifying coupler sub-unit tip surface 20 and the material edge 27 are placed and remain in compression.

Figure 23:
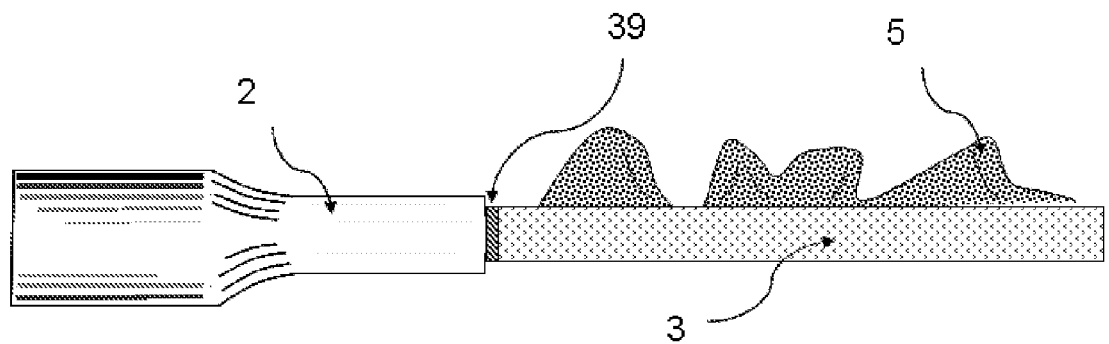
FIG. 23 is a side view of an amplifying coupler sub-unit connected to material via an adhesive bond, in accordance with a preferred embodiment of the present invention.

As shown in FIG. 23, the amplifying coupler sub-unit tip surface 20 and material edge 27 could be glued together with an adhesive 39. During the adhesive application process, the amplifying coupler sub-unit tip surface 20 and the material edge 27 would be preferably placed in compression with each other and held in place until the adhesive 39 cures. After the adhesive 39 cures, the two surfaces would be held in place by the adhesive 39 with longitudinal mechanical vibration and/or shock pulse motion transferring from the amplifying coupler sub-unit 2 into the material 3 through the adhesive. This similar process could be used to attach the converter sub-unit surface 15 to the amplifying coupler sub-unit surface 17.

Figure 24:
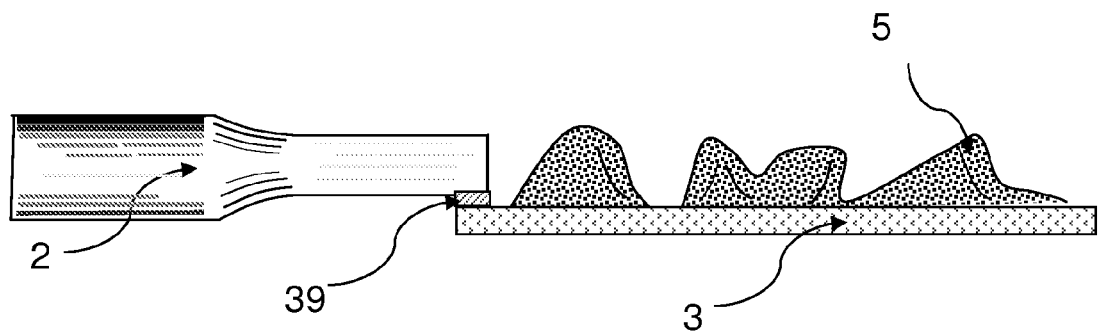
FIG. 24 is a side view of an amplifying coupler sub-unit with an offset connection to material via an adhesive bond, in accordance with a preferred embodiment of the present invention.

As shown in FIG. 24, the amplifying coupler sub-unit 2 and material 3 could be glued together with an adhesive 39 along the side surfaces. During the adhesive process, the amplifying coupler sub-unit 2 and the material 3 would be placed in compression with each other and held in place until the adhesive 39 cured. After the adhesive 39 cures, the two surfaces would be held in place by the adhesive 39 with longitudinal mechanical vibration and/or shock pulse motion transferring from the amplifying coupler sub-unit 2 into the material 3 through the adhesive.

Figure 25:
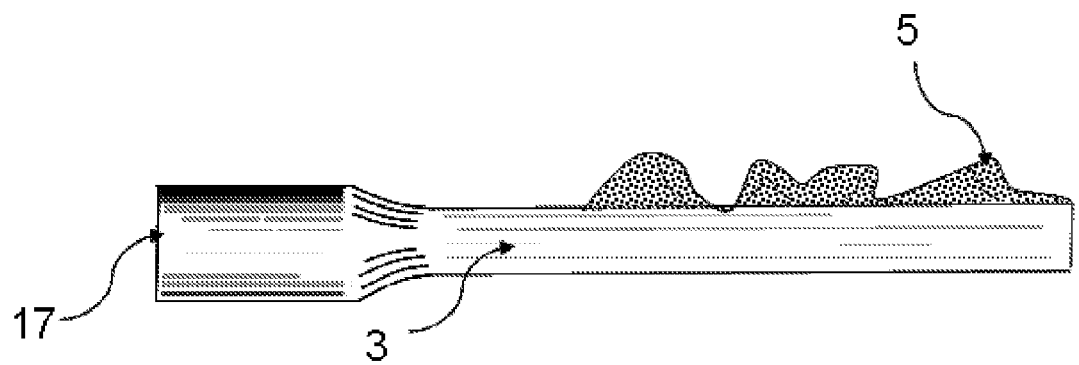
FIG. 25 is a side view of an amplifying coupler sub-unit and material formed integrally.

As a final example, shown in FIG. 25, the attachment or joint between the amplifying coupler sub-unit tip surface 20 and material edge 27 could be made nonexistent by forming the amplifying coupler sub-unit 2 and the material 3 from a single piece of material 3.

In any case, it is nonetheless advantageous to ensure a good attachment exists between the amplifying coupler sub-unit tip surface 20, which is experiencing longitudinal mechanical vibration and/or shock pulse motion 19, and the material edge 27. In a preferred embodiment, the amplifying coupler tip sub-unit surface 20 and the material edge 27 substantially remain in compression or have a strong adhesive 39 joint between them.

Figure 26:
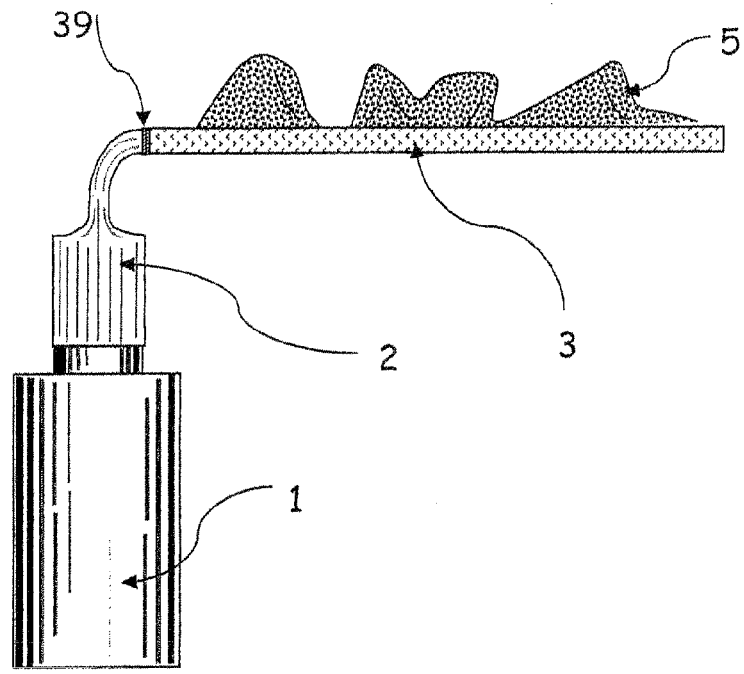
FIG. 26 is a top schematic view of an amplifying coupler sub-unit redirecting mechanical motion from a converter sub-unit.

An additional feature of the amplifying coupler sub-unit 2, as shown in FIG. 26, is that it can be designed to direct the longitudinal mechanical vibration and/or shock pulse motion developed by the converter sub-unit 1 in a direction and/or plane of reference which is not the same as the longitudinal mechanical vibration and/or shock pulse motion in the material 3.

6.0 Amplifying Coupler Sub-Unit to Material Surface Material Matching

In addition to ensuring a good compressive or adhesive attachment between the amplifying coupler sub-unit tip surface 20 and the material edge 27, it is also advantageous to understand what impedance values exists between the materials used for the amplifying coupler sub-unit 2 and the material 3. By understanding the material impedances, the values of the stress wave reflection and stress wave transmission coefficients can be calculated at the interface of the amplifying coupler sub-unit tip surface 20 to material edge 27. The longitudinal vibration motion 19 of the amplifying coupler sub-unit tip surface 20 is transferred by a force from the amplifying coupler sub-unit tip surface 20 pushing up against the material edge 27. Since this force is acting through the cross sectional area of the amplifying coupler sub-unit tip surface 20, a stress state is present at this interface. An efficient matching process of the materials and area changes between the amplifying coupler sub-unit 2 and material 3 are similar as was described in section 3.0.

7.0 Material with Debris Attached

Figure 27:
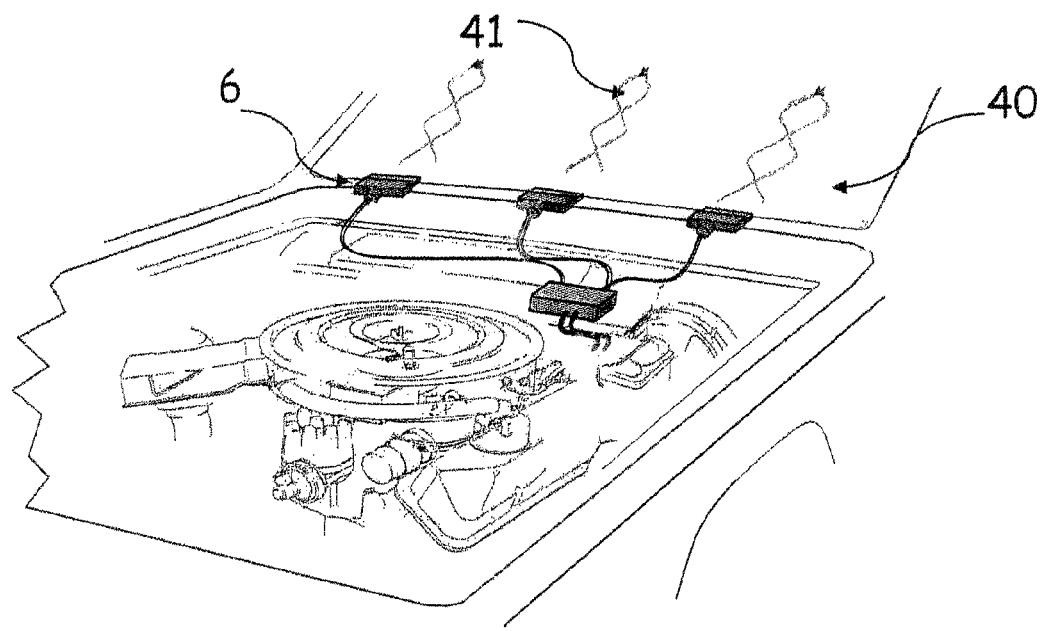
FIG. 27 is a perspective view illustrating three vibrating debris removers applied to an automobile windshield, in accordance with a preferred embodiment of the present invention.
Figure 28:
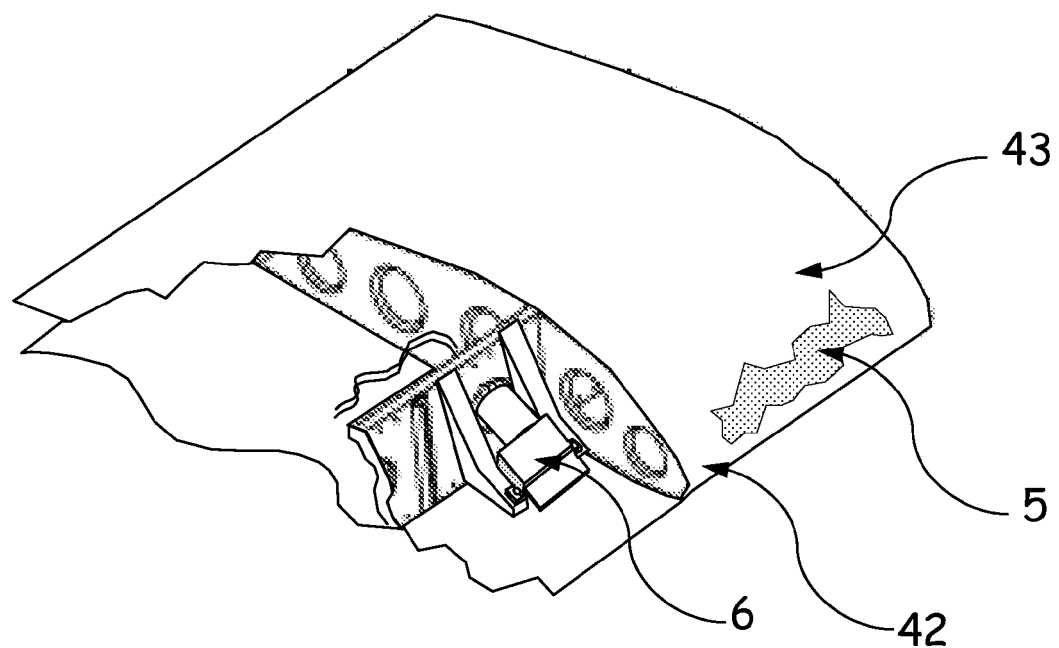
FIG. 28 is a perspective, partially cut-away view of a vibrating debris remover applied to an aircraft wing, in accordance with a preferred embodiment of the present invention.

The material 3 of interest has the debris 5 that is to be removed. For example, and as shown in FIG. 27, this material surface may serve the purpose of the windshield of an automobile 40 which is caused to vibrate 41 by the vibrating debris remover 6. It may also be the leading edge 42 of an aircraft wing 43 as shown in FIG. 28, or any of a plurality of other materials that may have debris attached. In any case, the existence of debris 5, such as ice and water, on the material 3 surface is not desired and is to be removed.

8.0 Designing an Efficient Vibrating System

In order that sufficient relative acceleration, strain, and strain rate can be achieved at the interface between the debris 5 and material 3, an efficient design must be developed. An efficient design for the vibrating debris remover 6 invention not only has to deal with the impedance matching of the converter sub-unit 1 to the amplifying coupler sub-unit 2 and the amplifying coupler sub-unit 2 to the material 3 of interest, but it also must be designed to vibrate with the least amount of energy 4 as possible while achieving the highest accelerations and strain rates in the material 3 and debris 5. This condition is known as resonance. Once the resonance state is achieved, the particle motions in the amplifying coupler sub-unit 2 and the material 3 of interest can have much greater amplitudes than the motions present in the material particles of the converter sub-unit 1. If low material damping is present, high Q or amplification values can be achieved. The result of high Q values is particle motion 36 and accelerations in the material 3 of interest which will cause the adhesive bond with the debris 5 particles to be broken.

To achieve resonance, the frequency of vibration of the converter sub-unit 1, amplifying coupler sub-unit 2, and the material 3 of interest must be the same (or within very close tolerance). Therefore, the operating frequency of the converter sub-unit 1 and the amplifying coupler sub-unit 2 must both be based on the frequency of a waveform traveling in the material 3.

Figure 20:
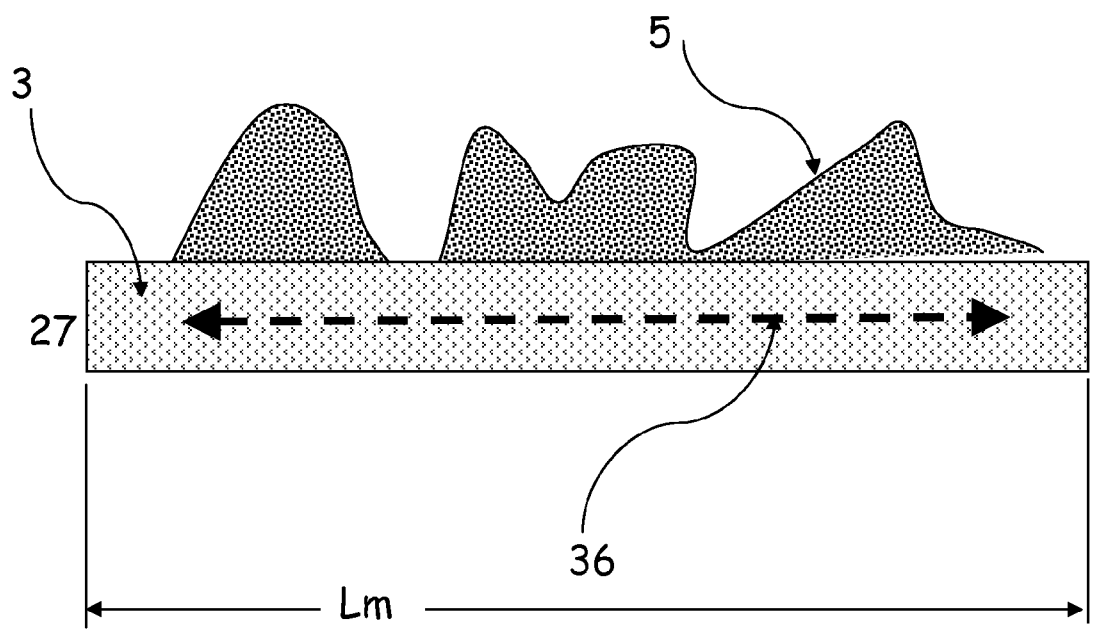
FIG. 20 is a schematic view of a material on which debris is attached.

Referring to FIG. 20, the fundamental frequency of vibration of a longitudinal wave in the material 3 can be calculated from mathematical equation (6).

$$f_m = \frac{v_m}{2L_m} \qquad \text{Equation (6)}$$

Where:

$f_m$=fundamental frequency of longitudinal wave in the material 3 (cycles/sec or Hz)

$v_m$=longitudinal sound velocity in material 3

$L_m$=length of the material 3

Once the vibration fundamental frequency of a longitudinal waveform in the material 3 has been determined, it is advantageous to determine the physical dimensions for the amplifying coupler sub-unit 2 such that it also wants to vibrate at the same frequency ($f_m$). In addition, the converter sub-unit 1 may be designed to operate at this same frequency ($f_m$).

Since the amplifying coupler sub-unit 2 is preferably to be designed to vibrate at the same or similar frequency as the material 3, and a stepped amplifying coupler sub-unit is easily manufactured, equation (7) has been derived to determine the required length ($l_c$ as shown in FIG. 17) of a stepped amplifying coupler sub-unit in order for it to vibrate at the same frequency ($f_m$) as the material 3. For a stepped amplifying coupler sub-unit in which the length of the larger cross sectional area ($a_c$ as shown in FIG. 17) is equal to one half of the total amplifying coupler sub-unit length ($a_c$=½ $l_c$ as shown in FIG. 17) the following equation can be developed:

$$\frac{S_a}{S_b}\sin\left(\frac{\pi l_c v_m}{2L_m v_c}\right)\cos\left(\frac{\pi l_c v_m}{2L_m v_c}\right) + \cos\left(\frac{\pi l_c v_m}{2L_m v_c}\right)\sin\left(\frac{\pi l_c v_m}{2L_m v_c}\right) = 0 \qquad \text{Equation (7)}$$

Where:

$v_m$=speed of sound in the material 3

$L_m$=length of material 3

$v_c$=speed of sound in the amplifying coupler sub-unit 2 material $l_c$=length of amplifying coupler sub-unit 2

$S_a$=cross sectional area of amplifying coupler sub-unit 2 larger end 17

$S_b$=cross sectional area of amplifying coupler sub-unit 2 smaller end 20

If proper impedance matching is performed between all materials and the vibrating debris remover 6 is designed to vibrate at the same frequency ($f_m$) as the material 3, then an energy efficient system will be developed.

9.0 Designing an Efficient Shock Pulse System

In order that sufficient relative acceleration, strain, and strain rate can be achieved at the interface between the debris 5 and material 3, an efficient design must be developed. The most efficient design for the shock pulse debris remover 6 invention not only has to deal with the impedance matching of the converter sub-unit 1 to the amplifying coupler sub-unit 2 and the amplifying coupler sub-unit 2 to the material 3 of interest, but the amplifying coupler sub-unit 2 should be designed to vibrate at a resonant frequency as the material of interest.

The frequency of vibration of the amplifying coupler sub-unit 2 and the material 3 of interest should be the same (or within close tolerance). The operating frequency of the amplifying coupler sub-unit 2 is based on the frequency of a longitudinal waveform traveling in the material 3 determined from equation 6. Once the vibration frequency of the waveform in the material 3 has been determined, it is advantageous to determine the physical dimensions for the amplifying coupler sub-unit 2 such that it also wants to vibrate at the same frequency. The process of designing a stepped amplifying coupler sub-unit for a vibrating system was described in Section 8.0 using equation (7). This exact same process is used to design a stepped amplifying coupler sub-unit for a shock pulse converter sub-unit 1. In fact, the amplifying coupler sub-unit designed in Section 8.0 is the exact same stepped amplifying coupler sub-unit designed for a shock pulse converter sub-unit 1

For a vibrating debris remover 6 designed to produce a shock pulse or multiple shock pulses, only the amplifying coupler sub-unit 2 has to be designed to vibrate at the same frequency as the material 3 for an energy efficient system to be developed, as was similarly done for the vibrating system.

10.0 Using the Converter Unit as a Debris Detector

Figure 29:
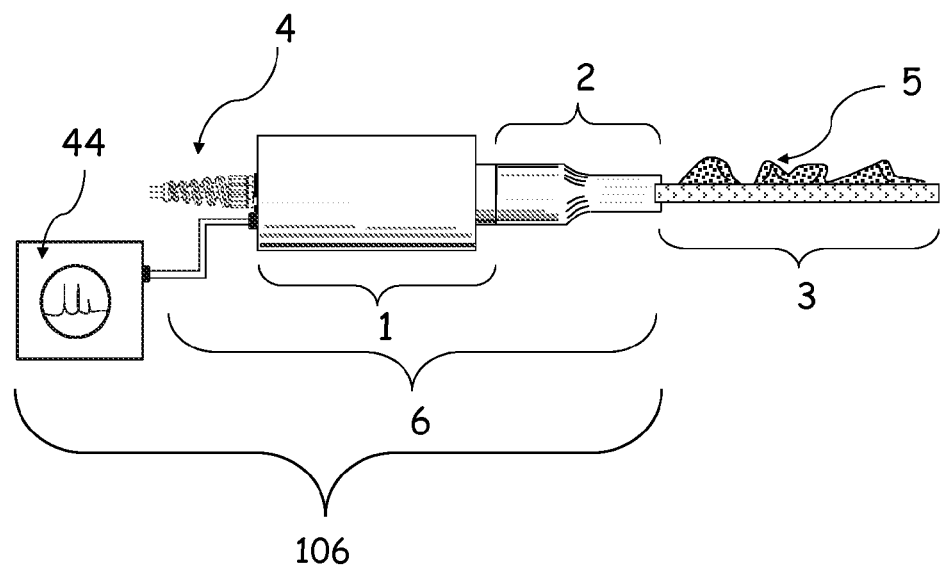
FIG. 29 is a side view of a vibrating debris remover with a pulser/receiver and/or spectrum frequency analyzer attached to the converter.

If the converter sub-unit 1 utilizes a piezoelectric crystal 16 to convert electrical energy 4 into mechanical motion 14, the converter sub-unit may also be attached to a pulser/receiver and/or a frequency spectrum electronic unit 44. A pulser/receiver is a device that that can generate electronic signals and receive electronic signals. A frequency spectrum electronic unit transforms a time history of an electronic signal into an electronic frequency spectrum. In such an embodiment, the assembly may alternatively or additionally be used as a debris detector 106, as shown in FIG. 29. The invented device may function as a debris detector 106 by either detecting vibration pulse delays as described in FIG. 30 and/or vibration spectrum frequency shifts, as described in FIG. 31.

Figure 30:
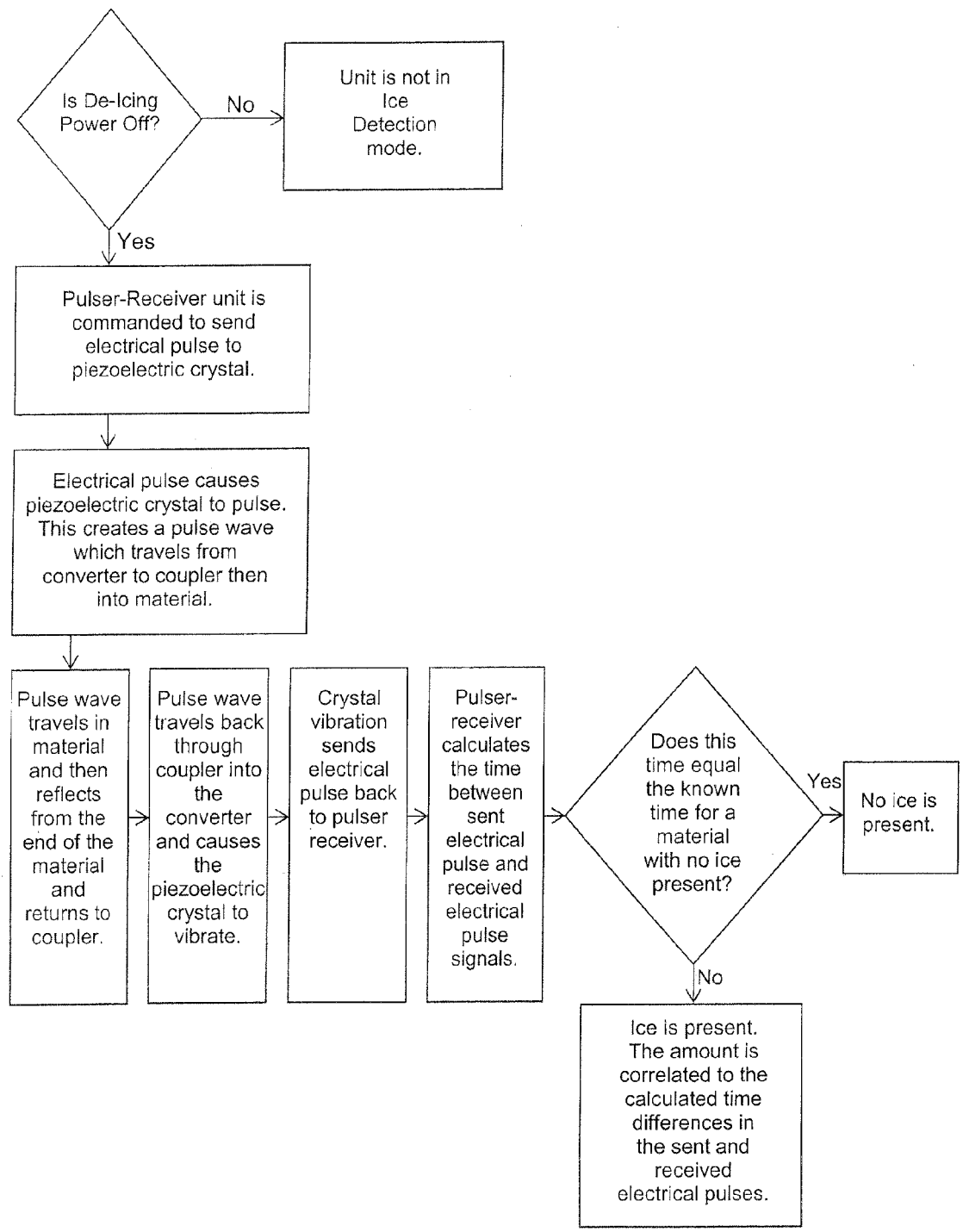
FIG. 30 is a flow chart illustrating how the vibrating debris remover may be used as a debris detector when used in conjunction with a pulser/receiver.

With reference to FIGS. 29-30, a pulser/receiver may be attached to vibrating debris remover 6 to form a debris detector 106. If the external energy source 4 were not turned on or was eliminated altogether, then a pulsed energy source similar to one shown in FIG. 7 could be sent to the piezoelectric crystals 16 by the pulser/receiver electronic unit 44. This unit 44 could be similar, without limitation, to those units used in material Non Destructive Evaluation testing (NDE), such as the RITEC RPR-4000 or the JSR DPR500 electronic units. Any other suitable pulser/receiver as known in the art is contemplated for use in this embodiment. The pulser/receiver 44 may cause the piezoelectric crystals 16 to pulse, causing mechanical motion to propagate into the material 3. This mechanical motion would reflect at the end of the material 3 and return to the piezoelectric crystals 16. This returning signal would cause the piezoelectric crystals 16 to vibrate. The piezoelectric crystal 16 vibrations may create an electrical signal which would be detected by the pulser/receiver electronic unit 44. The time delay between the pulsed signal and the received signal could then be measured. A known value of this time delay from a material 3 with no debris would be known and compared to the measured time delay. If this measured time delay were different from the measured time delay, then debris 5 would be present. The amount of debris 5 that is present on the material 3 surface may be determined based on the difference between the known time delay and the measured time delay. For example, the amount of debris present may be proportional to the difference between the known time delay and the measured time delay.

Figure 31:
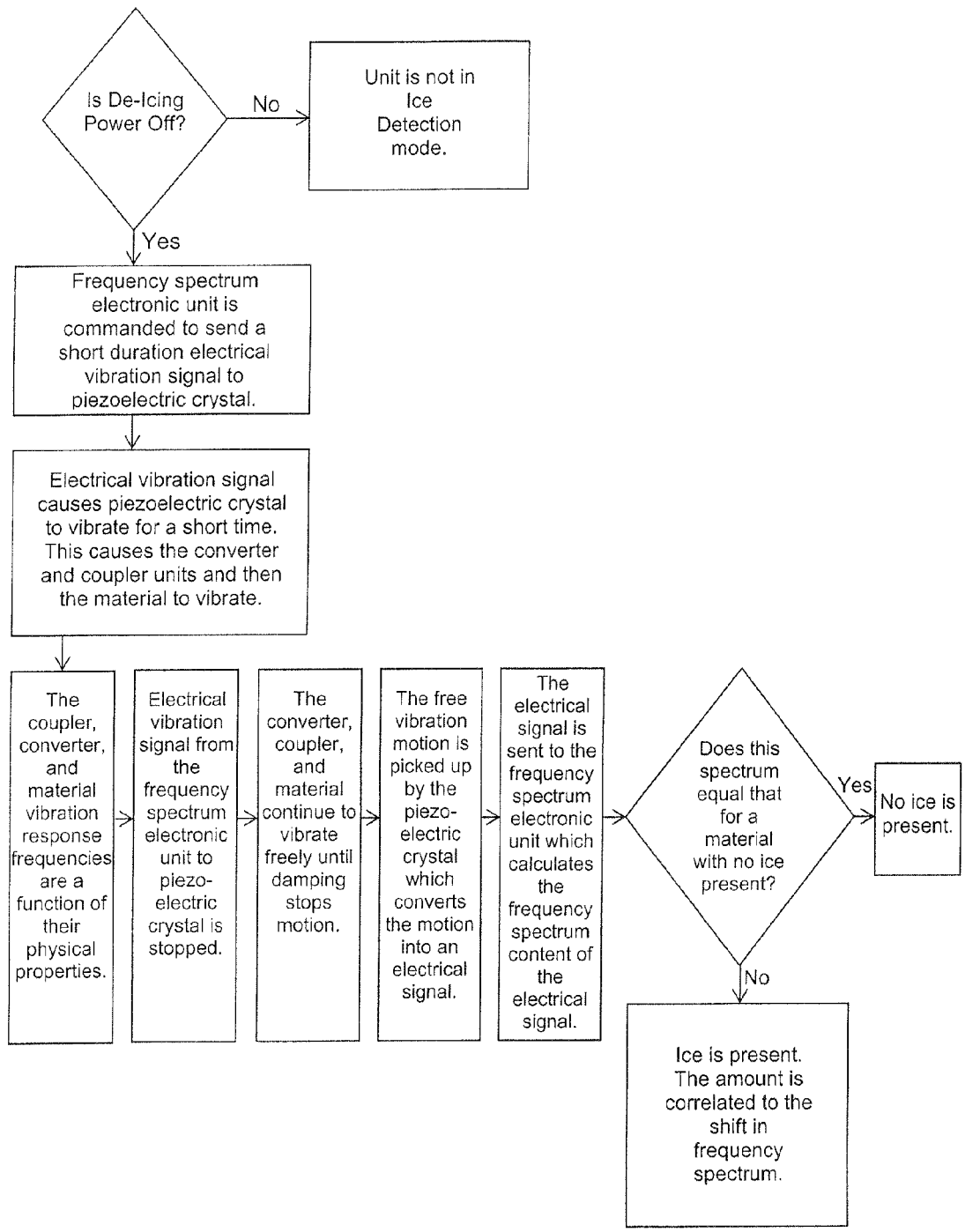
FIG. 31 is a flow chart illustrating how the vibrating debris remover may be used as a debris detector when used in conjunction with a frequency spectrum analyzer.

With reference to FIGS. 29 and 31, a frequency spectrum electronic unit 44 may be attached to vibrating debris remover 6 to form a debris detector 106. If the external energy source 4 were not turned on or was eliminated altogether, then a burst of vibratory excitation energy could be sent to the piezoelectric crystals 16 by the frequency spectrum electronic unit 44. This would cause the converter 1, coupler 2, and material 3 to vibrate. After this burst of excitation energy, the converter 1, coupler 2, and material 3 would continue to mechanically vibrate at resonant frequencies until structural damping stopped such vibration. This mechanical vibration would be detected by the piezoelectric crystals 16 which would convert this motion into an electrical signal and be sent to the pulser/receiver and/or frequency spectrum electronic unit 44. The electrical signal received by the frequency spectrum electronic unit 44 from the vibrating piezoelectric crystals 16 would be broken down into its frequency spectrum. A known value of this frequency spectrum from a material 3 with no debris would be known. If this measured frequency spectrum were different from the known value in either frequency and/or magnitude, then debris 5 would be indicated as present. The amount of debris present on the material 3 surface may be determined by the value of the difference in frequency and/or magnitude between the known frequency spectrum and measured frequency spectrum. For example, the amount of debris present may be proportional to the difference between the frequency and/or magnitude of the known frequency spectrum and the measured frequency spectrum. The principles, preferred embodiments and modes of operation of the present invention have been described in the forgoing application. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing detailed description should be considered exemplary in nature and not limited to the scope and spirit of the invention as set forth in the appended claims.

What is claimed is:

1. A method of detecting debris on a material, comprising the steps of:
   (a) providing a debris detector comprising:
      a piezoelectric converter unit that transforms electrical energy into mechanical motion at an output;
      a coupler having a first end and a second end, the first end being operably associated with the converter output so as to transmit the mechanical motion produced by the converter unit, the second end being attached to the material, and,
      a pulser/receiver operably connected to the converter unit, the pulser/receiver being operable to actuate the piezoelectric converter and receive electronic signals generated by the piezoelectric converter;
   (b) sending a first electronic signal from the pulser/receiver to activate the piezoelectric converter, thereby transmitting mechanical motion through the coupler and into the material;
   (c) receiving reflected mechanical motion through the coupler and into the converter, thereby generating a second electronic signal by the converter that is received by the pulser/receiver;
   (d) comparing an actual value associated with the second electronic signal to a known value.

2. The method of claim 1, wherein,
   the actual value associated with the second electronic signal is a measured time delay between the first electronic signal and the second electronic signal; and wherein the method further comprises:
   comparing the measured time delay to a known time delay measured with no debris attached to the material.

3. The method of claim 1, wherein,
   the actual value associated with the second electronic signal is a frequency spectrum of the second electronic signal, and wherein the method further comprises:
   comparing the measured frequency spectrum with a known frequency spectrum measured with no debris attached to the material.

4. The method of claim 1, wherein the known value is a value measured with no debris attached to the material.

5. The method of claim 1, wherein the material is a wing of an airplane.

6. The method of claim 1, wherein,
a cross-sectional area of the coupler at the first end is greater than a cross-sectional area of the coupler at the second end.

7. The method of claim 1, wherein the converter, coupler, and material each have an impedance, and the impedance of the coupler is substantially equal to the impedance of the material.

8. The method of claim 1, wherein the material, the coupler, and the converter each have at least one resonant frequency, the resonant frequency of the material being substantially equal to at least one of the resonant frequencies of the amplifying coupler and the converter.

9. The method of claim 1, wherein the material has a major dimension, and a minor dimension defining an edge, and wherein the second end of the coupler is associated with the edge of the material such that the coupler conducts mechanical motion into the material at an angle substantially perpendicular to the edge of the material.

* * * * *